US00PP28539P2

(12) United States Plant Patent
Kordes

(10) Patent No.: US PP28,539 P2
(45) Date of Patent: Oct. 24, 2017

(54) MINIATURE ROSE PLANT NAMED 'KORAROMA06'

(50) Latin Name: *Rosa hybrida*
Varietal Denomination: KORaroma06

(71) Applicant: W. Kordes Söhne Rosenschulen GmbH & Co. KG, Klein Offenseth-Sparrieshoop (DE)

(72) Inventor: Tim-Hermann Kordes, Klein Offenseth-Sparrieshoop (DE)

(73) Assignee: W. Kordes Söhne Rosenschulen GmbH & Co. KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 15/330,046

(22) Filed: Jul. 29, 2016

(51) Int. Cl.
*A01H 5/02* (2006.01)

(52) U.S. Cl.
USPC ..... Plt./121

(58) Field of Classification Search
USPC ..... Plt./121
CPC ..... A01H 5/022
See application file for complete search history.

*Primary Examiner* — Kent L Bell
(74) *Attorney, Agent, or Firm* — Samuel R. McCoy, Jr.

(57) ABSTRACT

'KORaroma06' is a new and distinct variety of *Rosa hybrida* which is characterized by the combination of a compact and bushy growth habit, a moderately vigorous rate of growth, good resistance to many rose diseases, panicles bearing five to six deep pink flowers, very double flowers, and strongly fragrant flowers. The new variety propagates successfully by stem cuttings and grafting and has shown to be uniform and stable in the resulting generations from asexual propagation.

1 Drawing Sheet

Latin name of genus and species: The Latin name of the genus and species of the novel variety disclosed herein is *Rosa hybrida.*

Variety denomination: The inventive variety of *Rosa hybrida* disclosed herein has been given the variety denomination 'KORaroma06'.

STATEMENT REGARDING PRIOR DISCLOSURES BY THE INVENTOR UNDER 37 C.F.R. 1.77(B)(6)

The first public disclosure of the claimed plant was made in January of 2016 at the 2016 IPM horticulture tradeshow in Essen, Germany where it was displayed by the inventor amongst a collection of other rose cultivars. The claimed plant was not specifically identified by name in the display. 'KORaroma06' was not publically available or sold prior to one year before the date of the instant application.

BACKGROUND OF THE INVENTION

Parentage: The *Rosa hybrida* variety 'KORaroma06' is the result of a controlled cross-pollination breeding program carried out by the inventor in Klein Offenseth-Sparrieshoop, Germany. The objective of the said breeding program was to create a new and distinct rose plant with unique qualities, such as:

1. A compact and bushy growth habit and uniform flowering when grown as a potted floral plant; and
2. Abundant, long-lasting, and recurrent deep pink flowers; and
3. Attractive foliage; and
4. Resistance to diseases encountered in greenhouse and nursery culture.

This combination of qualities is not present in prior rose cultivars known to the inventor. These objectives have been substantially achieved and in that distinguish 'KORaroma06' from all other varieties known to the inventor.

'KORaroma06' is a seedling selection which resulted from the controlled pollination of an unnamed *Rosa hybrida* seedling developed and owned by the same inventor, the seed parent, with *Rosa hybrida* 'KORpot028' (U.S. Plant Pat. No. 25,004), the pollen parent, during the summer of 2013. As part of a rose development program, Tim-Hermann Kordes germinated seeds from the aforementioned hybridization during the following winter and conducted evaluations and observations on the resulting seedlings in a controlled environment in Klein Offenseth-Sparrieshoop, Germany. The resulting seedlings exhibited distinctive physical and biological characteristics. The new rose plant was selected as a single plant in May of 2014 from the seedling beds due to its superior characteristics and asexually propagated for further evaluation. This new and distinctive rose variety was given the name 'KORaroma06'.

Asexual Reproduction: 'KORaroma06' was first asexually propagated by bud grafting in June of 2014 at the inventor's nursery in Klein Offenseth-Sparrieshoop, Germany. Subsequently, 'KORaroma06' has been successfully propagated by stem cuttings in Jackson County, Oreg. These initial and other subsequent propagations conducted in controlled environments demonstrate that 'KORaroma06' reproduces true to type in successive generations of asexual reproduction.

SUMMARY OF THE INVENTION

The following characteristics have been repeatedly observed and represent the distinguishing characteristics of the new *Rosa hybrida* cultivar 'KORaroma06'. These traits, in combination, distinguish 'KORaroma06' as a new and distinct cultivar.

1. *Rosa hybrida* 'KORaroma06' exhibits a moderately vigorous growth rate; and
2. *Rosa hybrida* 'KORaroma06' exhibits a compact, bushy growth habit; and
3. *Rosa hybrida* 'KORaroma06' exhibits good resistance to powdery mildew, blackspot and rust diseases; and
4. *Rosa hybrida* 'KORaroma06' exhibits panicles of 5 to 6 deep pink flowers held stiffly upright; and
5. *Rosa hybrida* 'KORaroma06' exhibits very double flowers of large size for a miniature rose; and
6. *Rosa hybrida* 'KORaroma06' exhibits flowers with strong fragrance.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORaroma06', taken from a one year old plant.

DETAILED BOTANICAL DESCRIPTION

The following is a detailed botanical description of a new and distinct variety of *Rosa hybrida* known as 'KORaroma06', based upon observations made in April of 2016 from one year old, greenhouse-grown container plants in Jackson County, Oreg. Those skilled in the art will appreciate that certain characteristics will vary with older or, conversely, with younger plants. 'KORaroma06' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2001 edition except where common terms of color are used.

A botanical description of 'KORaroma06' and comparisons with the parents and closest known comparator variety of *Rosa hybrida* are provided below.

General plant description:

*Growth rate*.—Moderately vigorous.

*Growth habit*.—Compact, bushy.

*Mature dimensions*.—25 cm tall and 20 cm wide, when grown as a 17 cm pot plant.

*Cold hardiness*.—Unknown.

*Propagation*.—Stem cuttings and bud grafting.

*Disease resistance*.—Good resistance to powdery mildew (*Sphaerotheca pannosa*), blackspot (*Diplocarpon rosae*), and rust (*Phragmidium* sp.) diseases under normal growing conditions in Jackson County, Oreg.

Root system:

*Type*.—Fibrous root system.

*Branching*.—Freely branched.

*Density*.—Moderately dense.

*Distribution*.—Roots distributed evenly throughout the soil profile, from shallow to deep.

Stems:

*Stem color*.—Young stems are Yellow-Green Group 146B; mature stems are Yellow-Green Group 146A.

*Anthocyanin intonations*.—Intonations of Greyed-Purple Group 187B are present on young stems.

*Stem surface texture*.—Both young stems and mature stems are smooth.

*Stem dimensions*.—Typical mature stems are approximately 35 cm long and 3 to 5 mm in diameter.

*Prickles*.—Incidence — Typically 5 prickles per 10 cm of stem, on average. Size — Average length is 4 mm long. Immature prickle color — Greyed-Red Group 181C. Mature prickle color — Greyed-Red Group 179C. Shape — Deeply concave. Texture — Smooth.

Leaves:

*Arrangement*.—Imparipinnate compound leaves; mature axillary leaves typically with 7 leaflets, yet leaves with 5 leaflets are regularly observed on the distal portion of stems.

*Attachment*.—Petiolate.

*Dimensions*.—125 mm long and 80 mm wide.

*Abundance*.—Very abundant; normally with 25 to 30 leaves.

*Stipules*.—Size — 15 mm long and 6 mm wide. Stipule color — Green Group 137C. Anthocyanin intonations — None. Stipitate glands — A limited number of stipitate glands are present on the abaxial surface and along the margins. Margins — With stipitate glands. Texture, adaxial surfaces — Glabrous. Texture, abaxial surfaces — Glabrous. Apex — Apiculate. Base — Winged.

*Petiole*.—Length — Average 8 mm. Diameter — Average 1.5 mm. Petiole color, adaxial surface — Yellow-Green Group 146B. Petiole color, abaxial surface — Yellow-Green Group 146C. Anthocyanin intonations — None. Margins — With occasional stipitate glands underneath and slight pubescence on the center rib. Prickles — None present. Stipitate glands — A very limited number of stipitate glands are present. Texture — Glabrous with the exception of the center rib which is slightly pubescent. Strength — Strong.

*Rachis*.—Length — Average 15 mm. Diameter — Average 1.5 mm. Color — Yellow-Green Group 146B. Anthocyanin intonations — Intonations of Greyed-Orange Group 176C are present on juvenile foliage. Margins — With sparse stipitate glands. Prickles — A few small prickles on the abaxial surface. Stipitate glands — A limited number of stipitate glands are present on the upper margin and also underneath at the point of leaf attachment. Texture — Glabrous with the exception of the center rib which is slightly pubescent.

*Leaflets*.—Dimensions — Average size of the terminal leaflet is 50 mm long and 35 mm wide. Shape — Ovate. Apex — Acute. Base — Obtuse. Margins — Finely serrated; no undulation. Texture, pubescence, and luster; adaxial surface — Smooth, glabrous, and semi-glossy. Texture, pubescence, and luster; abaxial surface — Smooth, glabrous, and matte. Juvenile foliage color, adaxial surface — Yellow-Green Group 146A. Juvenile foliage color, abaxial surface — Yellow-Green Group 146B. Mature foliage color, adaxial surface — Yellow-Green Group 147A. Mature foliage color, abaxial surface — Yellow-Green Group 147B. Anthocyanin intonations — Intonations of Greyed-Purple Group 185A to 185B are present on the center rib of both the adaxial and abaxial surfaces of the juvenile foliage. Venation — Reticulate. Petiolule — Dimensions — 3.0 mm long and 1.0 mm in diameter. Petiolule color, adaxial surface — Yellow-Green Group 146C. Petiolule color, abaxial surface — Yellow-Green Group 146D. Prickles — None observed. Margins — A few stipitate glands are present on the upper margins. Texture, adaxial surface — Smooth. Texture, abaxial surface — Smooth with a limited number of stipitate glands.

Inflorescence:

*Inflorescence type*.—Panicles which bear 5 to 6 flower buds. Flowers are held stiffly upright.

*Blooming habit*.—Recurrent; floriferous.

*Size*.—100 to 120 mm tall and 140 mm wide, on average.

*Peduncle*.—Length — 100 to 150 mm average length. Diameter — 3.0 to 5.0 mm average diameter. Color — Yellow-Green Group 146A. Anthocyanin intonations — None. Strength — Very strong. Surface — Smooth; glabrous.

Flowering laterals: Present below the initiation of inflorescence. Generally 1 to 2 flowering laterals are present, with 1 to 4 flowers per flowering shoot.

Flower bud:

*Bud form*.—Long; pointed ovoid.

*Size*.—Upon opening, 30 mm in length from base of receptacle to distal end of bud and 10 mm diameter at its widest point.

*Texture*.—Smooth.

*Color, as sepals first unfold*.—Red Group 47D.

*Color when one-quarter open, inner side*.—Red Group 53D.

*Color when one-quarter open, outer side*.—Red Group 53D.

*Color, outermost petals*.—Red Group 53D.

Flower:

*Pedicel*.—Length — 20 to 40 mm average length. Diameter — 2.0 to 3.0 mm average diameter. Color — Yellow-Green Group 146C. Anthocyanin intonations — None. Strength — Strong. Surface — Smooth, with very fine hairs and occasionally with a very limited number of stipitate glands.

*Calyx*.—General — Comprised of five polysepalous sepals, with moderate foliaceous appendages present on three sepals. Diameter of calyx — 55 mm, at anthesis. Sepals — Color, upper surface — Yellow-Green Group 146B to 146C. Color, lower surface — Yellow-Green Group 146B. Anthocyanin intonations — None. Size — 35 mm long and 12 mm wide, on average. Apex — Apiculate and cirrose. Base — Flat at union with receptacle. Quantity — Five. Upper surface — Moderately pubescent. Lower surface — With stipitate glands. Margins — Pubescent; stipitate glands are occasionally present. Stipitate glands, occurrence — Limited.

*Corolla*.—Habit — Very double. General shape of corolla — Cup-open; deep. Shape of corolla when viewed from the side — Upon opening, upper portion — Flat. Upon opening, lower portion — Flattened convex. Open flower, upper portion — Flat. Open flower, lower portion — Flattened convex. Dimensions — Large size for a miniature rose. When open, the average flower diameter is 90 mm and the average flower height is 45 mm. Fragrance — Strong fruity and myrrh fragrance. Duration — On the plant for 8 to 10 days; 3 to 5 days as a cut flower. Senesced petals drop away cleanly. Petals — Petal count — Exhibits very double flowers with an average of 80 to 90 petals under normal conditions. Petal reflex — Petals are slightly reflexed. Timing of petal reflex — Simultaneous. Petal margin — Entire. Petal shape — Obovate. Apex — Obtuse. Base — Cuneate. Dimensions — 25 to 45 mm long and 10 to 40 mm wide. Texture, inner surface — Smooth. Texture, outer surface — Smooth. Petal color, upon opening — Outermost petals, inner surface — Red-Purple Group N66C. Outermost petals, outer surface — Red-Purple Group N66C. Innermost petals, inner surface — Red-Purple Group 58B. Innermost petals, outer surface — Red-Purple Group 58B. Basal petal spots, upon opening — Outermost petals — Color, inner surface — Green-Yellow Group 1B. Color, outer surface — Yellow-Green Group 154D. Dimensions — 4 mm wide and 4 mm tall. Innermost petals — Color, inner surface — Green-Yellow Group 1D. Color, outer surface — White Group 155C. Dimensions — 4 mm wide and 5 mm tall. Petal color, after opening — Outermost petals, inner surface — Red-Purple Group 61C to 61D. Outermost petals, outer surface — Red-Purple Group 61D. Innermost petals, inner surface — Red Group 54B. Innermost petals, outer surface — Red-Purple Group 58C. Basal petal spots, after opening — Outermost petals — Color, inner surface — White Group 155A. Color, outer surface — White Group 155A. Dimensions — 7 mm wide and 5 mm tall. Innermost petals — Color, inner surface — White Group 155B. Color, outer surface — White Group 155B. Dimensions — 5 mm wide and 7 mm tall. General Tonality — On open flower, Red-Purple Group 58C. No change in general tonality at the end of the twelfth day; thereafter the general tonality is Red-Purple Group 58D. Petaloids — Quantity — 15 petaloids per flower, on average. Dimensions — Variable; approximately 5 to 20 mm long and 4 to 10 mm wide. Color, inner surface — Red Group 53D. Color, outer surface — Red Group 53D. Margins — Highly irregular; undulated to indented. Shape — Ovate to obovate. Apex — Variable from cuspidate to obtuse. Base — Attenuate. Texture, inner and outer surfaces — Smooth.

Reproductive organs:

*Stamens*.—Quantity — Approximately 120, on average, arranged around the styles. Anthers — Shape — Reniform. Dimensions — 3.0 mm long and 1.0 mm wide, on average. Color — Yellow-Orange Group 20B. Pollen — Absent. Filaments — Color — Yellow-Green Group 154D with intonations of Red Group 53C on the upper half. Length — 5 mm.

*Pistils*.—Quantity — Average; approximately 35. Stigmas — Size — Less than 1.0 mm. Location — Slightly inferior to equal in position to anthers. Color — Red Group 53C with tips Greyed-Yellow 161D. Styles — Length — Approximately 4.0 mm long. Color — White Group 155A, with intonations of Red Group 53C. Ovary — Dimensions — 4 mm long and 3 mm in diameter. Color — Green-White Group 157A.

*Receptacle*.—Shape — Urn-shaped. Dimensions — Approximately 14 mm high and 10 mm wide.

Color — Yellow-Green Group 146C. Texture — Smooth; glabrous.

Hips and seed formation: Not observed.

COMPARISONS WITH THE PARENTS

The new rose plant may be distinguished from its seed parent, an unnamed *Rosa hybrida* seedling, by the following combination of characteristics:

1. 'KORaroma06' exhibits deep pink flowers, whereas the seed parent exhibits cream apricot flowers.
2. 'KORaroma06' exhibits flowers of medium size for a miniature rose, whereas the seed parent exhibits large flowers.
3. 'KORaroma06' exhibits a moderately long shelf life as a potted plant, whereas the seed parent exhibits a short shelf life as a potted plant.

The new rose plant may be distinguished from its pollen parent, *Rosa hybrida* 'KORpot028', by the following combination of characteristics:

1. 'KORaroma06' exhibits deep pink flowers, whereas the pollen parent exhibits red flowers.
2. 'KORaroma06' exhibits flowers with strong fragrance, whereas the flowers of the pollen parent are non-fragrant.
3. 'KORaroma06' exhibits a moderately long shelf life as a potted plant, whereas the pollen parent exhibits an excellent, extended shelf life as a potted plant.

COMPARISON WITH THE MOST SIMILAR *ROSA* CULTIVAR KNOWN TO THE INVENTOR

For a comparison, several physical characteristics of the *Rosa hybrida* variety 'KORpot042', unpatented, a rose variety from the same inventor is compared to 'KORaroma06' in Chart 1.

CHART 1

| Characteristic | 'KORaroma06' | 'KORpot042' |
|---|---|---|
| Bud color as sepals unfold. | Red Group 47D. | Red Group 50B. |
| Petal count. | 80 to 90. | 30 to 40. |
| Fragrance. | Strong. | Non-fragrant. |

That which is claimed:

1. A new and distinct variety of rose plant named 'KORaroma06', as described and illustrated herein.

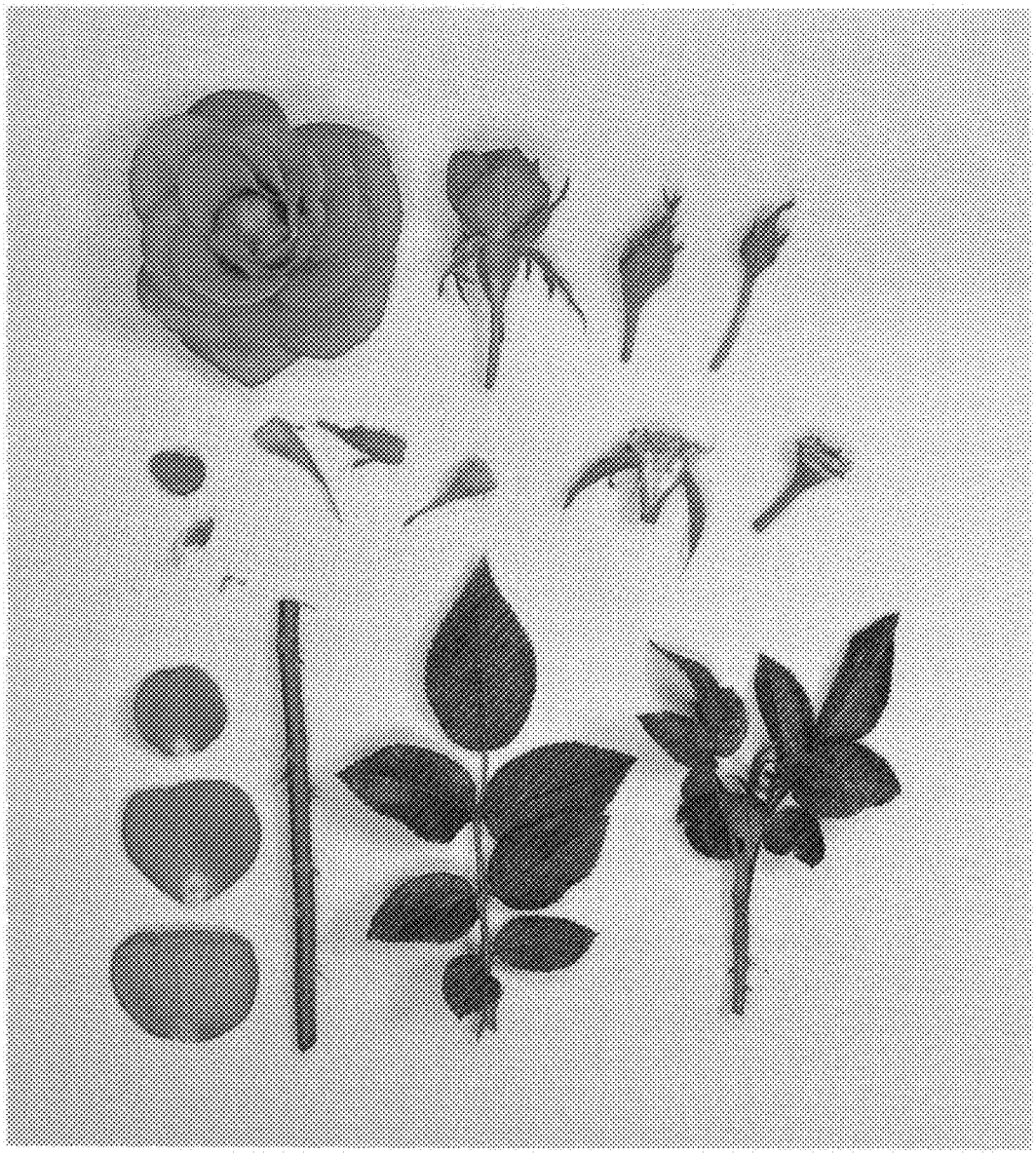

* * * * *